US00PP08286P

United States Patent [19]

Trees

[11] Patent Number: Plant 8,286

[45] Date of Patent: Jun. 29, 1993

[54] GERANIUM PLANT — BSR-194 CHERRY CULTIVAR

[75] Inventor: Scott C. Trees, Arroyo Grande, Calif.

[73] Assignee: George J. Ball, Inc., West Chicago, Ill.

[21] Appl. No.: 761,705

[22] Filed: Sep. 18, 1991

[51] Int. Cl.[5] ..... A01H 5/00
[52] U.S. Cl. ..... Plt./87.12
[58] Field of Search ..... Plt./87.12

*Primary Examiner*—James R. Feyrer
*Assistant Examiner*—E. F. McElwain
*Attorney, Agent, or Firm*—Burns, Doane, Swecker & Mathis

[57] ABSTRACT

A new and distinct tetraploid *Pelargonium*×*hortorum* cultivar named BSR-194 Cherry is provided. This new Zonal Geranium cultivar was the result of a controlled breeding program wherein an unnamed plant designated 535-5 was pollinated by the Veronica cultivar (U.S. Plant Pat. No. 5,054). The new cultivar forms attractive semi-double cherry red florets which contrast well with dark green zoned foliage. The attractive dark green foliage coloration is well retained even during shipment. The growth habit is inherently compact and self-branching and does not require the use of growth regulators to maintain such growth characteristic.

1 Drawing Sheet

SUMMARY OF THE INVENTION

The present invention comprises a new and distinct Geranium cultivar, botanically known as *Pelargonium*-×*hortorum*, and hereinafter is referred to by the cultivar name BSR-194 Cherry.

The new cultivar is the product of a planned breeding program which had as its objective the creation of a highly productive new Geranium cultivar which exhibits attractive red blossoms, dark green foliage, a compact self-branching growth habit, no requirement for the use of a growth regulator, a propensity for rapid rooting, and stable foliage coloration during shipment. This objective was satisfactorily fulfilled in the cultivar of the present invention.

The breeding program which resulted in the production of the new cultivar of the present invention was carried out in a controlled environment during 1989 at Santa Maria, Calif., U.S.A. The female parent (i.e., the seed parent) was an unnamed plant designated 535-5. Such female parent formed semi-double scarlet florets, formed dark green foliage, and was compact and self-branching. The male parent (i.e., the pollen parent) was the Veronica cultivar (U.S. Plant Pat. No. 5,054). Such male parent formed semi-double cherry-purple florets, formed medium green foliage, and exhibited good weather tolerance. The parentage of the new cultivar can be summarized as follows:

535-5×VERONICA.

The seeds resulting from the above pollination were sown and plantlets were obtained which were physically and biologically different from each other. Selective study which was finalized during December 1989, at Santa Maria, Calif. resulted in the identification of a single plant of the new cultivar. This plant initially was designated BSR-194.

It was found that the new cultivar of the present invention:

(a) exhibits attractive cherry red semi-double florets, (b) forms attractive dark green foliage which resists breakdown during shipment,
(c) bears zoned leaves, and
(d) exhibits an inherently compact and self-branching growth habit in the absence of growth regulators.

The new cultivar also is less tolerant to Botrytis blight than the Veronica and Atlantis cultivars.

Asexual reproduction of the new cultivar by vegetative cuttings initially taken on Feb. 9, 1990, and horticulturally examined in a controlled environment on Apr. 1, 1990, at Santa Maria, Calif., has demonstrated that the characteristics of the new cultivar as herein described are firmly fixed and are retained through successive generations of asexual propagation.

When plant material of the BSR-194 Cherry cultivar is subjected to standard random amplified polymorphic DNA marker analysis (RAPD) using polymerase chain reaction (PCR) and a known unique set of DNA primers, it is found to exhibit a distinctive fingerprint map which is on file at the Ball Flora Plant Division of George J. Ball, Inc. at Arroyo Grande, Calif.

BSR-194 Cherry has not been observed under all possible environmental conditions to date. Accordingly, it is possible that the phenotype may vary somewhat with variations in the environment, such as temperature, light intensity, and day length.

When the new cultivar of the present invention is compared to the Atlantis cultivar (U.S. Plant Patent pending), The BSR-194 Cherry cultivar is observed to exhibit a somewhat darker blossom coloration, and dark green foliage which exhibits a more yellow-green coloration as specified in greater detail hereinafter. Also, the peduncle coloration at the base tends to be Yellow-Green Group 144A for the new cultivar vs. Green Group 140B for the Atlantis cultivar.

The new cultivar of the present invention is being marketed under the Showcase trademark.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at Santa Maria, Calif.

DETAILED DESCRIPTION

The chart used in the identification of colors described herein is The R.H.S. Colour Chart of The Royal Horticultural Society, London, England. Color terminology in common terms precedes the reference to The R.H.S. Colour Chart information. The color values were determined on Jul. 18, 1991 at 2:00 to 3:00 p.m. using a light intensity of 1300 footcandles at Santa Maria, Calif. The plants described were grown under standard greenhouse conditions.

Classification:

*Botanical.*—*Pelargonium*×*hortorum,* cv. BSR-194 Cherry.

*Commercial.*—Zonal Geranium.

INFLORESCENCE

A. Umbel:

*Average diameter.*—Approximately 10 to 11 cm.

*Average depth.*—Approximately 5 to 6 cm.

*Peduncle length.*—Approximately 15 to 19 cm.

*Pedicel length.*—Approximately 2.75 to 3 cm.

When five month old plants are grown in the field, the BSR-194 Cherry cultivar commonly possesses approximately 28 to 30 umbels per plant while the Atlantis cultivar commonly possesses approximately 20 to 25 umbels per plant. Such field grown plants commonly possess approximately 30 to 32 florets per umbel for the BSR-194 Cherry cultivar and approximately 18 to 25 florets per umbel for the Atlantis cultivar.

B. Corolla:

*Average diameter.*—Approximately 4.5 to 5.0 cm. This can be compared to approximately 4.7 to 5.0 cm. for the Atlantis cultivar.

*Form.*—Semi-double. The three bottom petals commonly are imbricate and measure approximately 2.4 cm. in length and approximately 2.2 cm. in width, the two upper petals commonly are non-imbricate and measure approximately 2.8 cm. in length and approximately 1.4 cm. in width, and the smaller petaloids commonly number approximately 2 to 4 and range in length from approximately 0.6 to 2.0 cm. In contrast the florets of the Atlantis cultivar commonly possess approximately 3 to 4 bottom outer petals which measure approximately 2.3 cm. in length and approximately 2.0 cm. in width, approximately 2 upper outer petals which measure approximately 2.6 cm. in length and approximately 1.7 cm. in width, and approximately 3 inner smaller petaloids which range from approximately 1.0 to 1.8 cm. in length.

*Color (general tonality from a distance of* 3 *meters)*-.—Cherry red, Red Group 47B.

*Color (abaxial).*—Upper two petals exhibit Red Group 45A on the edges, an eye of Red-Purple Group 61C in the middle, and a base of Red Group 43A; and the bottom petals exhibit Red Group 45A. This can be compared to Red Group 46C for the Atlantis cultivar.

*Color (adaxial).*—Red Group 44A. This can be compared to Red Group 50A for the Atlantis cultivar.

The petals of the BSR-194 cultivar commonly display three distinct shades of cherry red and orange while the petals of the Atlantis cultivar commonly display a single dark cherry red coloration.

C. Bud:

*Shape.*—Upright, in a hemispheroidal cluster.

*Color (abaxial).*—Red Group 45A.

*Color (adaxial).*—Red Group 44A.

D. Reproductive organs:

*Androecium.*—The anthers commonly are approximately 2.5 to 3 mm. in length and are Red Group 43B in coloration. The pollen is red-orange in coloration, Red Group 40A; and the filaments commonly are of an irregular configuration. Some petaloids commonly are present.

*Gynoecium.*—The pistil length commonly is approximately 7 to 8 mm., there is a single stigma which commonly branches into 6 parts, and the style length is approximately 3 to 4 mm.

*Fertility.*—Commonly does not produce fruits in the absence of mechanical fertilization.

E. Spring flowering response period: Approximately 5 to 6 weeks from rooted cuttings under greenhouse conditions maintained at 55° F. at night and 72° F. during the day when potted on March 1st in a soil mix (e.g., Sunshine No. 2 brand soil mix) in 10 cm. pots.

F. Outdoor flower production: Continuous blooming.

G. Durability: The dark green foliage is stable and does not break down during shipment. Not as tolerant to Botrytis blight as the Veronica and Atlantis cultivars.

PLANT

A. Foliage: Darker zoning at the outer margin of the leaves.

*Form.*—Reniform, cordate base.

*Margin.*—Crenate.

*Color (abaxial).*—Dark green, Yellow-Green Group 147A at the outer margins or zones (e.g., outer 1 to 1.5 cm.) and Green Group 137A at the center of the leaves. This compares to a coloration of Green Group 132A for the Atlantis cultivar.

*Color (adaxial).*—Green Group 137B having veins of Green Group 137D. This compares to a coloration of Green Group 135B for the Atlantis cultivar.

B. General Appearance and form:

*Internode length.*—Commonly varies from approximately 2 to 3 cm.

*Branching pattern.*—Self branching.

*Height.*—Approximately 20 to 25 cm. above a 10 cm. pot when the blossoms first open. The BSR-194 Cherry cultivar is distinctly more compact and basal branching when grown in a pot or in the field that the Atlantis cultivar. No pinching or the use of growth regulator is required to obtain compact and self-branching plants of the BSR-194 Cherry cultivar. However, the Atlantis cultivar commonly exhibits a non-branching upright growth habit unless it is pinched or treated with growth regulators.

I claim:

1. A new and distinct cultivar of Geranium plant named BSR-194 Cherry, substantially as herein shown and described, which:

(a) exhibits attractive cherry red semi-double florets, (b) forms attractive dark green foliage which resists breakdown during shipment, (c) bears zoned leaves, and (d) exhibits an inherently compact and self-branching growth habit in the absence of growth regulators.

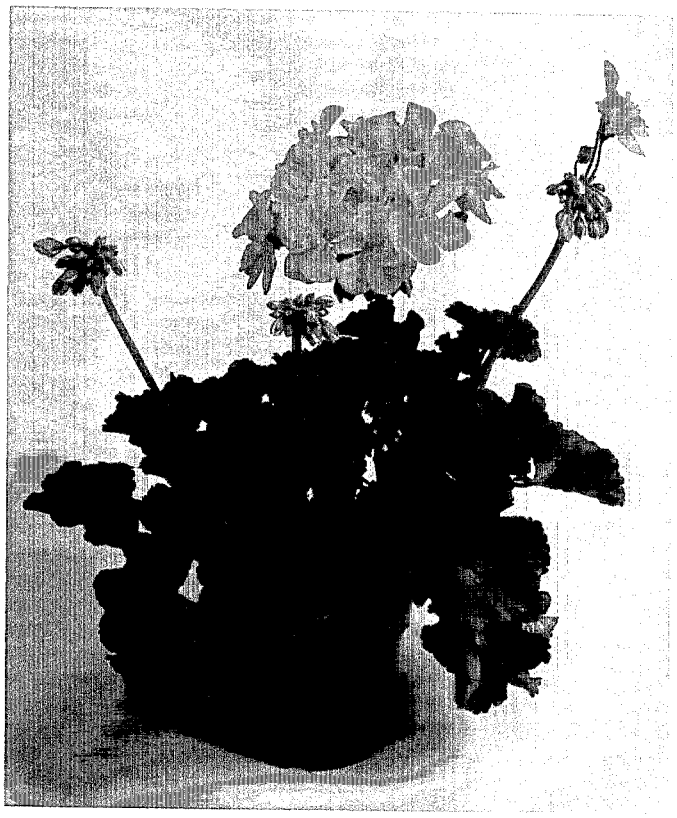

* * * * *